United States Patent
Burkett (10) Patent No.: US 10,537,715 B2
(45) Date of Patent: Jan. 21, 2020

(54) PRESSURE GUIDE WIRE PULLBACK CATHETER

(71) Applicant: Volcano Corporation, San Diego, CA (US)

(72) Inventor: David H. Burkett, Temecula, CA (US)

(73) Assignee: VOLCANO CORPORATION, San Diego, CA (US)

( * ) Notice: Subject to any disclaimer, the term of this patent is extended or adjusted under 35 U.S.C. 154(b) by 878 days.

(21) Appl. No.: 14/845,066

(22) Filed: Sep. 3, 2015

(65) Prior Publication Data

US 2016/0067456 A1 Mar. 10, 2016

Related U.S. Application Data

(60) Provisional application No. 62/046,010, filed on Sep. 4, 2014.

(51) Int. Cl.
| | |
|---|---|
| *A61B 5/0215* | (2006.01) |
| *A61M 25/09* | (2006.01) |
| *A61B 5/02* | (2006.01) |
| *A61B 5/00* | (2006.01) |
| *A61M 25/00* | (2006.01) |

(52) U.S. Cl.
CPC ......... *A61M 25/09* (2013.01); *A61B 5/02007* (2013.01); *A61B 5/0215* (2013.01); *A61B 5/6852* (2013.01); *A61B 5/742* (2013.01); *A61M 25/005* (2013.01); *A61M 25/007* (2013.01); *A61B 2560/0475* (2013.01)

(58) Field of Classification Search
CPC .. A61M 25/09; A61M 25/005; A61M 25/007; A61M 2025/0003; A61M 2025/0002; A61M 2025/09175; A61B 5/02007; A61B 5/0215; A61B 5/6851; A61B 5/6852; A61B 5/742; A61B 19/54; A61B 2560/0475; A61B 2562/0247
USPC ....... 600/485, 486, 488, 462, 465, 505, 549, 600/561
See application file for complete search history.

(56) References Cited

U.S. PATENT DOCUMENTS

| | | | | |
|---|---|---|---|---|
| 5,300,085 | A * | 4/1994 | Yock | A61B 18/245 604/103.04 |
| 5,450,853 | A * | 9/1995 | Hastings | A61B 5/0215 600/488 |
| RE35,648 | E * | 11/1997 | Tenerz | A61B 5/0215 600/374 |

(Continued)

*Primary Examiner* — Navin Natnithithadha (57) ABSTRACT

Intravascular devices, systems, and methods are provided. In some embodiments, the intravascular devices are catheters with a plurality of openings in a distal portion to facilitate taking pressure measurements from within a lumen of the catheter. The intravascular device includes a tubular member that has a proximal portion and a distal portion; a lumen extending from the proximal portion to the distal portion along a longitudinal axis of the tubular member, the lumen sized and shaped to receive a pressure sensing device; and openings spaced along the distal portion of the tubular member, the openings sized and shaped to provide fluidic communication between the lumen and a region surrounding the tubular member to allow the pressure sensing device to measure an ambient pressure of the region surrounding the tubular member from within the lumen. An intravascular system and a method for obtaining pressure measurements are also provided.

19 Claims, 4 Drawing Sheets

(56) References Cited

U.S. PATENT DOCUMENTS

| | | | | |
|---|---|---|---|---|
| 5,935,120 | A * | 8/1999 | Williams | A61M 25/0026 604/500 |
| 5,964,714 | A * | 10/1999 | Lafontaine | A61B 5/0215 600/561 |
| 6,162,182 | A * | 12/2000 | Cole | A61B 5/0215 600/486 |
| 6,461,332 | B1 * | 10/2002 | Mosel | A61B 5/202 600/29 |
| 6,514,236 | B1 * | 2/2003 | Stratienko | A61M 25/0041 604/508 |
| 6,579,266 | B2 * | 6/2003 | Mosel | A61B 5/202 600/29 |
| 6,585,660 | B2 * | 7/2003 | Dorando | A61B 5/0215 128/920 |
| 6,743,165 | B2 * | 6/2004 | Mosel | A61B 5/202 600/30 |
| 7,222,539 | B2 * | 5/2007 | Tulkki | A61B 5/0215 73/756 |
| 8,192,366 | B2 * | 6/2012 | Mauge | A61B 5/031 600/486 |
| 8,216,151 | B2 * | 7/2012 | Smith | A61B 5/6851 600/485 |
| 8,231,537 | B2 * | 7/2012 | Ahmed | A61B 5/02158 600/485 |
| 8,277,386 | B2 * | 10/2012 | Ahmed | A61B 5/02158 600/488 |
| 8,282,566 | B2 * | 10/2012 | Mauge | A61B 5/031 600/488 |
| 8,641,633 | B2 * | 2/2014 | Smith | A61B 5/6851 600/485 |
| 8,668,650 | B2 * | 3/2014 | Ehr | A61B 5/02007 600/486 |
| 9,113,790 | B2 * | 8/2015 | Ehr | A61B 5/02007 |
| 9,247,909 | B2 * | 2/2016 | Meyer, Jr. | A61B 5/6851 |
| 9,259,161 | B2 * | 2/2016 | Suchecki | A61B 5/02007 |
| 9,717,472 | B2 * | 8/2017 | Ahmed | A61B 8/06 |
| 9,770,225 | B2 * | 9/2017 | Ahmed | A61B 8/445 |
| 9,775,567 | B2 * | 10/2017 | Suchecki | A61B 5/02007 |
| 9,826,910 | B2 * | 11/2017 | Burkett | A61B 5/0215 |
| 9,913,585 | B2 * | 3/2018 | McCaffrey | A61B 5/02158 |
| 2003/0120175 | A1 * | 6/2003 | Ehr | A61B 5/02007 600/561 |
| 2005/0187487 | A1 * | 8/2005 | Azizkhan | A61B 5/0215 600/561 |
| 2006/0211944 | A1 * | 9/2006 | Mauge | A61B 5/031 600/488 |
| 2006/0211945 | A1 * | 9/2006 | Mauge | A61B 5/031 600/488 |
| 2006/0211946 | A1 * | 9/2006 | Mauge | A61B 5/031 600/488 |
| 2007/0060834 | A1 * | 3/2007 | Odland | A61B 5/0215 600/561 |
| 2009/0156960 | A1 * | 6/2009 | Mauge | A61B 5/031 600/561 |
| 2013/0102927 | A1 * | 4/2013 | Hilmersson | A61B 5/0215 600/585 |
| 2013/0296718 | A1 * | 11/2013 | Ranganathan | A61B 5/02 600/481 |
| 2014/0005543 | A1 | 1/2014 | Burkett | |
| 2014/0183670 | A1 * | 7/2014 | Millett | B81C 1/0023 257/415 |
| 2014/0187979 | A1 * | 7/2014 | Burkett | A61B 5/6847 600/486 |
| 2014/0187986 | A1 * | 7/2014 | Ehr | A61B 5/02007 600/486 |
| 2015/0196210 | A1 * | 7/2015 | McCaffrey | A61B 5/02158 600/488 |
| 2015/0359445 | A1 * | 12/2015 | Ehr | A61B 5/02007 600/487 |
| 2016/0249821 | A1 * | 9/2016 | Boye | A61B 5/0215 600/424 |

* cited by examiner

PRESSURE GUIDE WIRE PULLBACK CATHETER

CROSS REFERENCE TO RELATED APPLICATIONS

The present application claims priority to and the benefit of the U.S. Provisional Patent Application No. 62/046,010, filed Sep. 4, 2014, which is hereby incorporated by reference in its entirety.

TECHNICAL FIELD

The present disclosure relates generally to intravascular devices, systems, and methods. In some embodiments, the intravascular devices are catheters with a plurality of openings in a distal portion to facilitate taking pressure measurements from within a lumen of the catheter.

BACKGROUND

Heart disease is very serious and often requires emergency operations to save lives. A main cause of heart disease is the accumulation of plaque inside the blood vessels, which eventually occludes the blood vessels. Common treatment options available to open up the occluded vessel include balloon angioplasty, rotational atherectomy, and intravascular stents. Traditionally, surgeons have relied on X-ray fluoroscopic images that are planar images showing the external shape of the silhouette of the lumen of blood vessels to guide treatment. Unfortunately, with X-ray fluoroscopic images, there is a great deal of uncertainty about the exact extent and orientation of the stenosis responsible for the occlusion, making it difficult to find the exact location of the stenosis. In addition, though it is known that restenosis can occur at the same place, it is difficult to check the condition inside the vessels after surgery with X-ray.

A currently accepted technique for assessing the severity of a stenosis in a blood vessel, including ischemia causing lesions, is fractional flow reserve (FFR). FFR is a calculation of the ratio of a distal pressure measurement (taken on the distal side of the stenosis) relative to a proximal pressure measurement (taken on the proximal side of the stenosis). FFR provides an index of stenosis severity that allows determination as to whether the blockage limits blood flow within the vessel to an extent that treatment is required. The normal value of FFR in a healthy vessel is 1.00, while values less than about 0.80 are generally deemed significant and require treatment.

Often intravascular catheters and guide wires are utilized to measure the pressure within the blood vessel. To date, guide wires containing pressure sensing devices have suffered from reduced performance characteristics compared to standard guide wires that do not contain such pressure sensing devices. Existing pressure guide wires typically have a single pressure sensing device located approximately 3 cm from the distal tip of the guide wire. The sensors are fixed in position. Thus, to take pressure readings at multiple locations along the blood vessel, the physician must re-cross a distal lesion.

Accordingly, there remains a need for improved intravascular devices, systems, and methods.

SUMMARY

Intravascular devices, systems, and methods are provided. In some instances, the devices, systems, and methods include a catheter with a plurality of openings in a distal portion to facilitate taking pressure measurements from within a lumen of the catheter.

According to embodiments disclosed herein, an intravascular device may include a tubular member. The tubular member may have a proximal portion and a distal portion; a lumen extending from the proximal portion to the distal portion along a longitudinal axis (LA) of the tubular member, the lumen sized and shaped to receive a pressure sensing device; and openings spaced along the distal portion of the tubular member, the openings sized and shaped to provide fluidic communication between the lumen and a region surrounding the tubular member to allow the pressure sensing device to measure an ambient pressure of the region surrounding the tubular member within the lumen.

According to some embodiments, a system may include an intravascular device and a pressure sensing device. The intravascular device may include a tubular member. The tubular member may have a proximal portion and a distal portion; a lumen extending from the proximal portion to the distal portion along a longitudinal axis of the tubular member; and openings spaced along the distal portion of the tubular member, the openings sized and shaped to provide fluidic communication between the lumen and a region surrounding the tubular member. The pressure sensing device may be sized and shaped to translate within the lumen of the intravascular device.

According to some embodiments, a method for obtaining pressure measurements from an intravascular environment may include disposing an intravascular device inside a blood vessel; advancing a pressure sensing device through a lumen of the intravascular device to a position within a distal portion of the intravascular device; and obtaining pressure measurements with the pressure sensing device positioned within the distal portion of the intravascular device.

These and other embodiments of the present invention will be described in further detail below with reference to the following drawings.

BRIEF DESCRIPTION OF THE DRAWINGS

In the figures, elements having the same reference number have the same or similar functions.

DETAILED DESCRIPTION

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

As used herein, "tubular member" includes at least any thin, long, flexible structure that can be inserted into the vasculature of a patient. While the illustrated embodiments of the "tubular members" of the present disclosure have a cylindrical profile with a circular cross-sectional profile that defines an outer diameter of the tubular member, in other instances all or a portion of the tubular members may have other geometric cross-sectional profiles (e.g., oval, rectangular, square, elliptical, etc.) or non-geometric cross-sectional profiles. Tubular members include, for example, guide wires and catheters.

The tubular member is sized and shaped to allow for its diameter to be very small. As such, the tubular member of the present application is suitable for use in a wide variety of lumens within a human patient besides those that are part or immediately surround the heart, including veins and arteries of the extremities, renal arteries, blood vessels in and around the brain, and other lumens.

"Connected" and variations thereof as used herein includes direct connections, such as being glued or otherwise fastened directly to, on, within, etc. another element, as well as indirect connections where one or more elements are disposed between the connected elements.

"Secured" and variations thereof as used herein includes methods by which a member is directly secured to another element, such as being glued or otherwise fastened directly to, on, within, etc. another element, as well as indirect techniques of securing two elements together where one or more elements are disposed between the secured elements.

Figure 1:
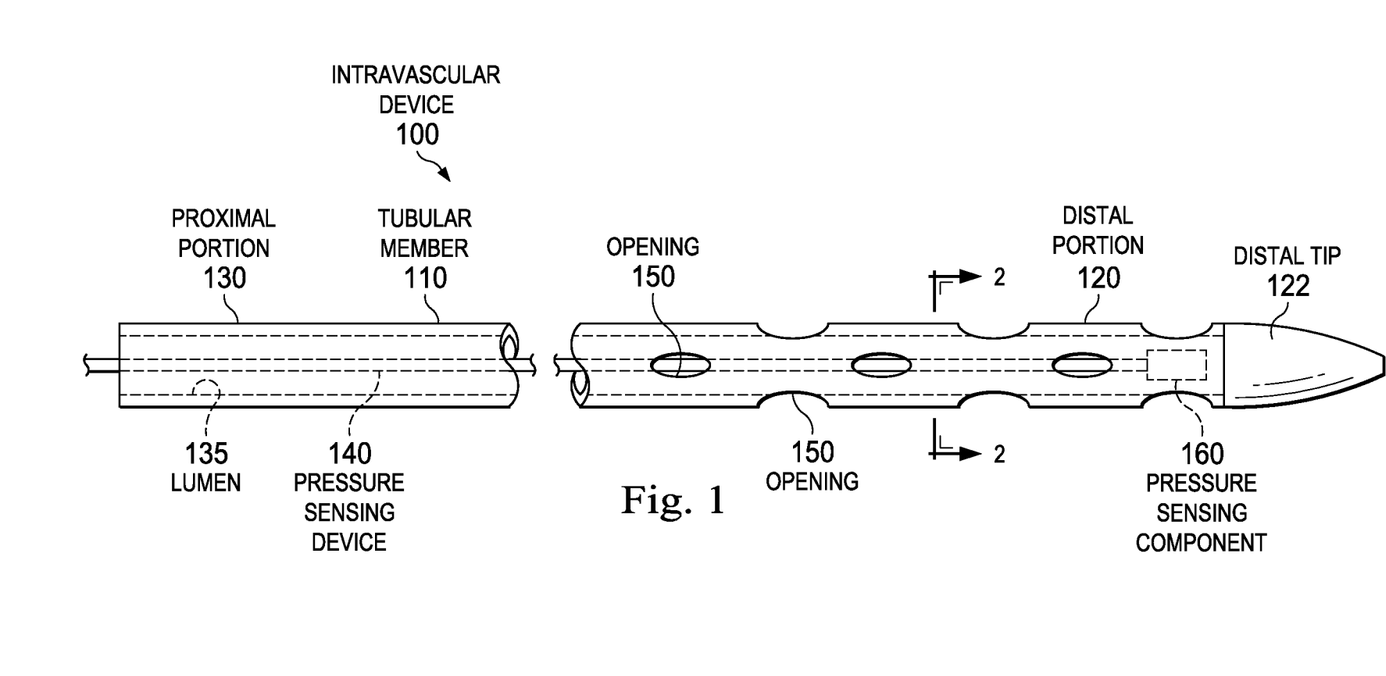
FIG. 1 is a diagrammatic, schematic side view of an intravascular device, according to some embodiments.

FIG. 1 is a diagrammatic, schematic side view of intravascular device 100, according to some embodiments. The intravascular device 100 includes a tubular member 110. The tubular member 110 has a distal portion 120 adjacent a distal tip 122 and a proximal portion 130. Generally, the proximal portion 130 is configured to be positioned outside of a patient, while the distal portion 120 is configured to be inserted into the patient, including within human vasculature. The total length of tubular member 110 can be any suitable length. In some embodiments the total length is between about 1100 mm and about 4000 mm, with some specific embodiments having a length of 1400 mm, 1900 mm, and 3000 mm. Tubular member 110 in the illustrated embodiment is a thin-walled cylindrical body with a lumen 135 sized to receive a pressure sensing device 140. The illustrated tubular member includes a plurality of openings 150 spaced along the distal portion 120. As shown, a component 160 (e.g., a sensor) is secured to a portion of the pressure sensing device 140. The pressure sensing component 160 can include electrical (e.g. resistive), optical, fluid column, and/or other suitable pressure sensing arrangements.

Embodiments consistent with the present disclosure provide the ability to push and retract the pressure sensing device 140 to multiple locations along the length of the tubular member 110 without repositioning the tubular member 110 within the blood vessel. For example, pressure sensing device 140 may slide relative to tubular member 110 along a longitudinal axis. In some embodiments, the pressure sensing device 140 slides inside the lumen 135 of the tubular member 110. Accordingly, the diameter of the lumen 135 may be larger than an outer diameter of the pressure sensing device 140 to accommodate for movement within the tubular member 110. In that regard, the diameter of the lumen 135 may be between 0.0005 inches and 0.010 inches, or larger in some implementations. To that end, the pressure sensing device 140 may have an outer diameter of 0.014 inches, 0.018 inches, and 0.035 inches in some instances.

The position of the distal tip 122 of the tubular member 110 can remain fixed within the vessel while the pressure sensing device 140 is moved through the lumen 135. Embodiments of the pressure sensing device 140 may include markings or other indicators identifiable via external imaging to provide an indication of the location of the pressure sensing device 140 relative to the vessel and/or the tubular member 110. Accordingly, in some embodiments the markings provide reference positions that correlate to the relative position of component 160 to the tubular member 110. Thus, a physician may know precisely how far the pullback of the pressure sensing device 140 has proceeded. Markings may be configured to be identifiable using an external imaging modality such as x-ray, fluoroscopy, CT scan, or MRI. Embodiments of the pressure sensing device 140 may also include, but are not limited to, those previously disclosed by Volcano Corporation, such as those disclosed in U.S. patent application Ser. No. 13/931,052 which was filed on Jun. 28, 2013, now published as U.S. Patent Application Publication No. 2014/0005543 on Jan. 2, 2014 and entitled "Intravascular Devices, Systems, and Methods," the contents of which are herein incorporated by reference in their entirety, for all purposes.

The distal tip 122 may be secured to or integrally formed with the tubular member 110. In some embodiments, the distal tip 122 may be secured to the distal portion of the tubular member 110 via adhesive, solder, or laser weld. In the illustrated embodiment, the distal tip 122 is a soft tip that tapers as it extends distally toward the distal end to provide a tapered lead for tracking. A soft tip aids in vessel navigation and reduces the risk of vessel injury. The total length of distal tip 122 can be any suitable length from 0.1 cm to 5 cm. In particular instances, distal tip 122 may be about 1 cm in length. In some embodiments, distal tip 122 may include a radiopaque material such that distal tip 122 is identifiable under x-ray, fluoroscopy, and/or other imaging modalities when positioned within a patient.

Figure 2:
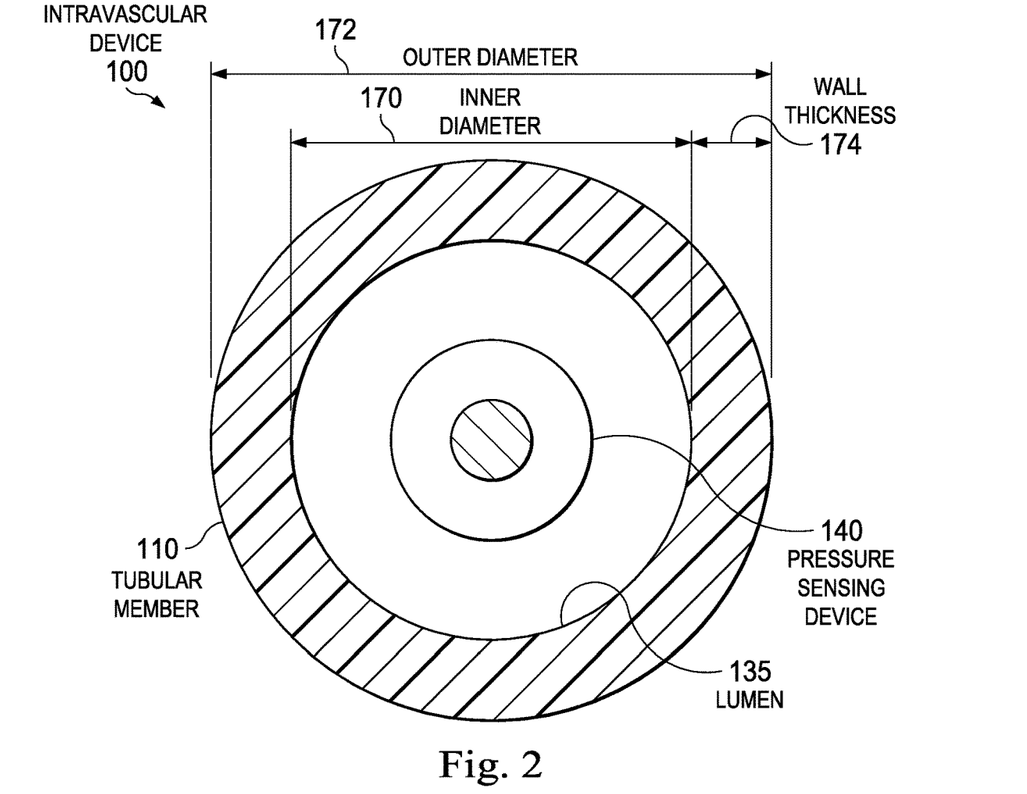
FIG. 2 is a side view of a portion of an intravascular device including an opening, according to some embodiments.

FIG. 2 is a diagrammatic cross-sectional end view of intravascular device 100 taken along section line 2-2 of FIG. 1, according to some embodiments. The tubular member 110 as has an inner diameter 170, an outer diameter 172, and a wall thickness 174. In the illustrated embodiment, the wall thickness 174 of the tubular member 110 is uniform. In some embodiments, the wall is a minimum thickness to reduce the impact of the catheter on flow through a stenosis. In some embodiments, the wall thickness 174 of the tubular member 110 may vary. The tubular member 110 includes the lumen 135 as an inner recess defining the inner diameter 170. In some instances, the pressure sensing device 140 is a pressure-sensing guide wire with a diameter as large as it can be to still allow the guide wire to slide through the tubular member 110.

Figure 3:
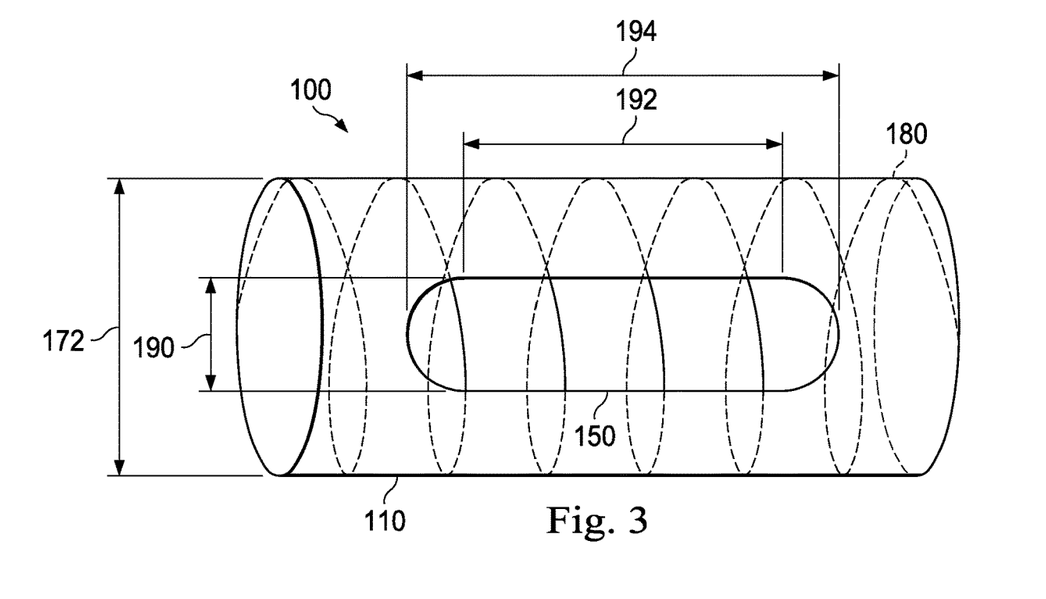
FIG. 3 is a diagrammatic cross-sectional end view of the intravascular device of FIG. 1 taken along section line 3-3, according to some embodiments.

FIG. 3 is a side view of a portion of the intravascular device 100 including an opening 150, according to some embodiments. The tubular member 110 of the intravascular device 100 may be constructed of polymers such as polyimide, Pebax, nylon, nitinol, or any other suitable biocompatible device material. In some embodiments, the tubular member 110 may be reinforced. Some particular embodiments have coiled, braided, and/or axial reinforcement. In some instances, a reinforcement element 180 is embedded within the polymer tubing. Reinforcing the polymer tubing can increase the tensile and compressive strength of the tubular member 110 and help prevent kinks in the tubular member 110. In some embodiments, the reinforcement element 180 is formed of stainless steel. In other embodiments, the reinforcement element 180 may be formed of other known materials, such as carbon fibers or nitinol. The cross section of the reinforcement element may be round or rectangular in shape. Rectangular ribbon reinforcement elements may be 0.0005 inches thick by 0.0025 inches wide, but could be thicker/wider as desired.

In the illustrated embodiment, a spiral ribbon coil is used to reinforce the tubular member 110. Spiral reinforcement provides additional hoop strength to the tubing. Further, spiral reinforcement helps to maintain the cylindrical inner diameter shape of the tubular member 110 as the pressure sensing device 140 is retracted and pushed forward. Additionally, reinforcement of the tubular member 110 may consist of a thin ribbon braid. If braided, the braid geometry can provide adequate opening for pressure access. The spacing/pitch 182 of the ribbons or braided material may range from 0.001 inches to 0.010 inches, with particular embodiments ranging from 0.002 inches to 0.004 inches. The pitch of the reinforcement element may vary along the length of the tubular member. Reinforcement of tubular member 110 may also consist of axial reinforcement such as individual ribbon wires running longitudinally and embedded in the polymer tubing. In some embodiments, the reinforcement element extends the entire length of the tubular member 110. Alternatively, the reinforcement element of the tubular member 110 may be located only in the distal section, only in the proximal section, or in portions thereof.

In embodiments where the tubular member 110 is a polymer tubing embedded with spiral ribbon 180, the tubular member 110 may have an outer diameter 172 as small as 0.017 inches, an inner diameter 170 of 0.015 inches, and a corresponding wall thickness 174 of approximately 0.001 inches. In embodiments where the tubular member 110 is a polymer tubing embedded with a thin ribbon braid, the tubular member 110 may have an outer diameter as small as 0.019 inches, an inner diameter of 0.015 inches, and a corresponding wall thickness 174 of approximately 0.002 inches. The small outer diameter of the tubular member minimizes impact on flow/pressure across lesions. In other embodiments, the wall thickness of the tubular member may be non-uniform.

In some embodiments, the inner and outer surfaces of the tubular member 110 are impregnated with polytetrafluoroethylene (PTFE). Coating the inner surface with PTFE provides a lubricious surface that reduces friction between the pressure sensing device 140 and the inner wall of the tubular member 110. Further, the PTFE impregnated outer surface allows the tubular member 110 to move more freely within the vessel walls, which improves trackability and navigation.

Additionally, FIG. 3 shows an opening 150 through a sidewall of tubular member 110. Opening 150 in the illustrated embodiment is generally pill shaped, having elongated straight sides oriented along the longitudinal axis of the tubular member 110 and rounded ends. In that regard, the opening 150 has a height 190 that is generally between about 25% and about 60% of the tubular member's outer diameter 172. In some embodiments, overall opening height 190 ranges from 0.002 inches to 0.010 inches, with some specific embodiments having a height ranging from 0.004 inches to 0.008 inches. In one particular embodiment, the tubular member 110 has a diameter 172 of 0.020 inches and opening 150 has a height 190 of 0.006 inches.

In the illustrated embodiment, the straight sidewalls of the opening 150 have a length 192, while the opening 150 has an overall length 194 that extends from the opening's proximal most portion to the opening's distal most portion. In some embodiments, overall length 194 ranges from 0.005 inches to 0.040 inches, with some specific embodiments having a length ranging from 0.007 inches to 0.015 inches. The size and shape of the opening 150 ensures that the component 160, such as a sensor, has access to the ambient pressure outside the intravascular device. The length 192 of the sidewalls of the opening 150 can be between 10% and 99% of the overall length 194 of the opening 150.

In embodiments where the tubular member 110 includes spiral, braided, or axial reinforcement element, the portions of the reinforcement element extending across the opening 150 may be removed. In some instances, the opening 150 may be formed by chemically dissolving a section of the side wall of the tubular member 110. Additionally, opening 150 may be formed by laser cutting the side wall of the tubular member 110. Alternatively, the reinforcement element may remain intact across the opening 150. By leaving the reinforcement element intact, better strength can be provided and any concerns about the cut edges of the reinforcement element material injuring the patient can be eliminated.

Geometry of opening 150 is not restricted to a certain shape. In some embodiments, the opening 150 may have a circular, oval, or slotted shape. The shape illustrated in FIG. 3 increases tolerance for sensor positioning while maintaining tubing integrity. In some embodiments, opening 150 may be formed by smaller openings. Access to pressure is made via the openings and/or the spacing/pitch of the ribbon coils. Spacing of the openings 150 is dependent upon application constraints and desired accessibility to the surrounding environment in which the intravascular device 100 will be used.

Figure 4:
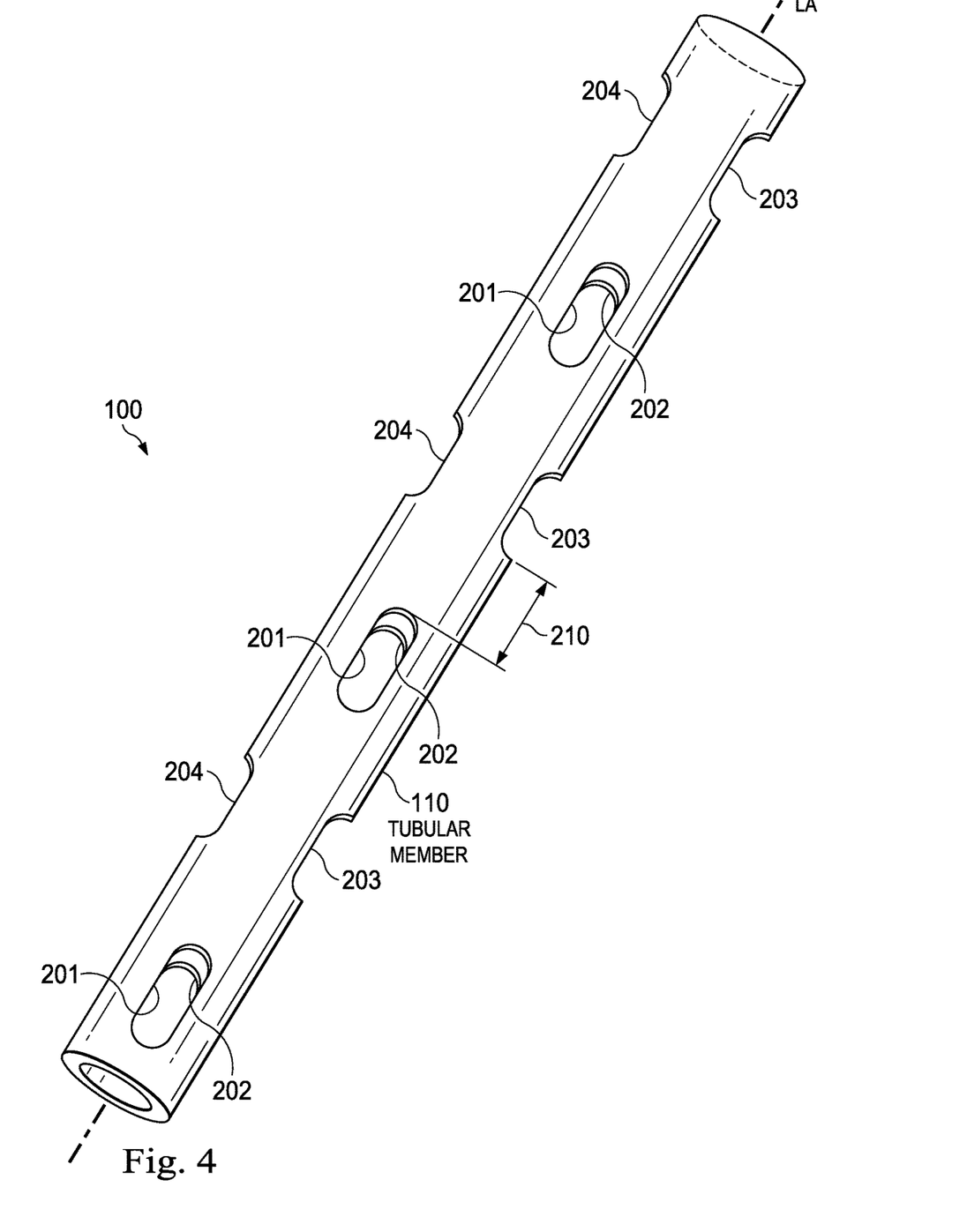
FIG. 4 is a perspective view of a portion of an intravascular device including a plurality of openings in a pattern, according to some embodiments.

FIG. 4 is a perspective view of a portion of intravascular device 100 including a plurality of openings in a pattern, according to some embodiments. A pressure sensing device may have fluidic contact with blood and other tissue elements in a vessel's interior through openings in tubular member 110. The openings provide portals that enable the pressure sensing device to access blood and other tissue elements in a vessel's interior at different locations along the longitudinal axis. For example, the openings may allow for access to vessel pressures at different locations along the longitudinal axis.

The plurality of openings may be configured in a pattern. The pattern can be selected to ensure that intravascular pressure is accessible even when one side of the tubular member 110 is up against a vessel wall. The openings in FIG. 4 show a first pattern of openings 201, a second pattern of openings 202, a third pattern of openings 203, and a fourth pattern of openings 204. As shown in FIG. 4, the openings extend linearly along the longitudinal axis and are spaced at regular intervals. The patterns are repeated along a desired length to provide continuous pressure access for pullback of the pressure sensing device. In the illustrated embodiment, the first pattern 201, the second pattern 202, the third pattern 203, and the fourth pattern 204 are equally spaced about the circumference of the tubular member. In FIG. 4, the first pattern 201 and the second pattern 202 of openings align. Similarly, the third pattern 203 and the fourth pattern 204 of openings align. The first pattern 201 and the second pattern 202 of openings are linearly offset from the third pattern 203 and the fourth pattern 204 of openings by a distance 210. Distance 210 may be 0 to 5 cm, with some specific embodiments having a distance of 1 mm to 5 mm.

In some embodiments, other patterns may be used. The pattern of openings can be any pattern that will provide adequate resolution along a desired length of tubular member 110. In some examples, the patterns may be circumferentially offset from each other by an angle other than 90°. Some embodiments may include more or less than four patterns of openings, for example a fifth pattern of openings. In some instances, the openings may be spaced at irregular intervals. Other embodiments may include a single pattern of openings that spirals around the tubular member.

Figure 5:
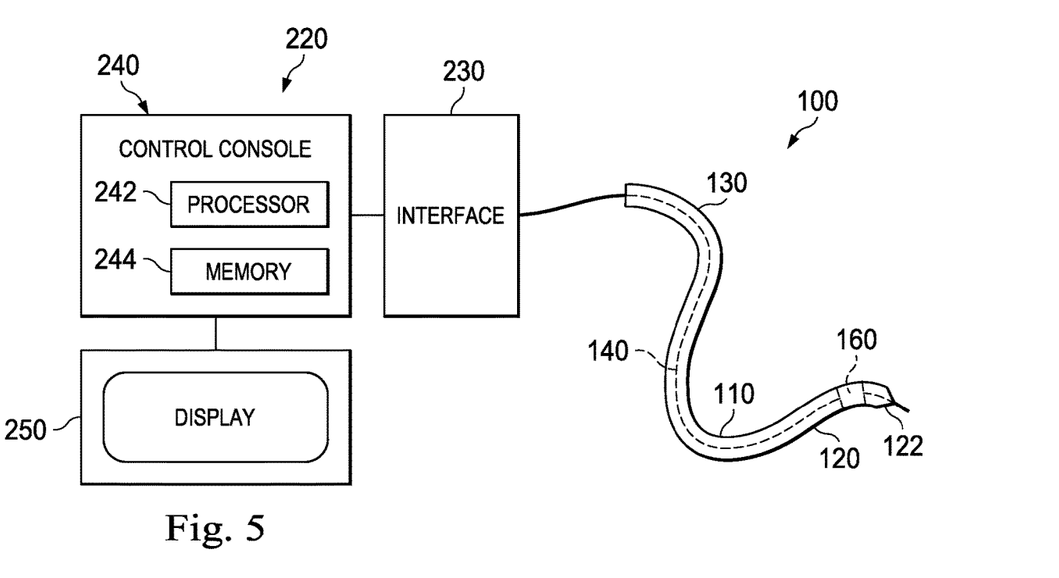
FIG. 5 is a schematic view of an intravascular system, according to some embodiments.

FIG. 5 is a schematic view of a system 220 for performing measurements using an intravascular device 100 according to some embodiments. System 220 may include an intravascular device 100 and a pressure sensing device 140. Intravascular device 100 may include a tubular member 110 having a proximal portion and a distal portion; a lumen extending from the proximal portion to the distal portion along a longitudinal axis of tubular member 110; and openings spaced along the distal portion of the tubular member 110 (e.g., proximal portion 130, distal portion 120, and openings 150, cf. FIG. 1). The openings may be sized and shaped to provide fluidic communication between the lumen and a region surrounding the tubular member.

The pressure sensing device 140 may be sized and shaped to translate within the lumen 135 of the intravascular device 100. In some embodiments, the pressure sensing device 140 is a guide wire. In some particular embodiments, the guide wire has an outer diameter of approximately 0.014 inches, 0.018 inches, or 0.035 inches. The distal portion of pressure sensing device 140 may include a component 160, such as a sensor.

Additionally, FIG. 5 shows an interface device 230; a control console 240; and a display unit 250. In the illustrated embodiment, the control console 240 includes a processor circuit 242 and a memory circuit 244. The interface device 230 may be configured to interface with a proximal portion of the pressure sensing device 140. For example, the interface device 230 may be coupled to the proximal end of the pressure sensing device 140.

The interface device 230 may include electronic circuits configured to provide power and signals to pressure sensing device 140. Electronic circuits in the interface device 230 may also be configured to receive and process signals from the pressure sensing device 140. For example, the interface device 230 may include an analog to digital converting circuit. Thus, the interface device 230 may perform analog-to-digital conversion of signals provided by the pressure sensing device 140. The console 240 may control the operation of interface device 230 by providing power and receiving the sensor circuit data processed by interface device 230. The operation of the console 240 may be performed by the processor circuit 242 executing commands stored in the memory circuit 244. Once the data is processed and further analyzed in the console 240, an image may be displayed in the display unit 250. For example, an image may include a graphic display and charts representing pressure values along a longitudinal direction in a blood vessel.

Figure 6:
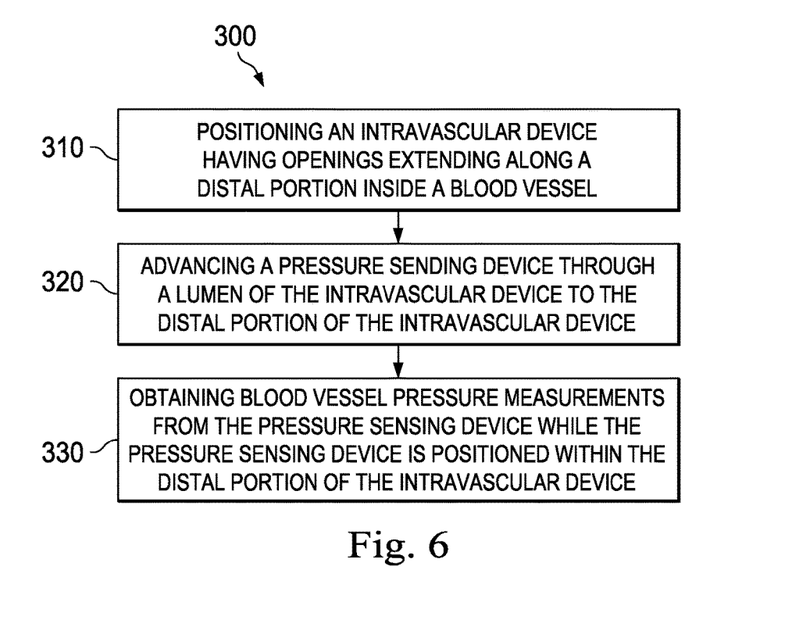
FIG. 6 is a flow chart of a method for obtaining pressure measurements from an intravascular environment, according to some embodiments.

FIG. 6 is a flow chart of a method 300 for obtaining measurements from an intravascular environment, according to some embodiments. Method 300 may be partially performed by an operator using a system for performing measurements with a pressure sensing device 140 exposed to an intravascular environment, as the system 220 described in detail above (cf. FIG. 5). The system in method 300 may include an intravascular device and a pressure sensing device (e.g., intravascular device 100 and pressure sensing device 140, c.f. FIG. 5). Intravascular device may include a tubular member having a proximal portion and a distal portion; a lumen extending from the proximal portion to the distal portion along a longitudinal axis of the tubular member; and openings spaced along the distal portion of the tubular member (e.g., tubular member 110, proximal portion 130, distal portion 120, and openings 150, cf. FIG. 1). The openings may be sized and shaped to provide fluidic communication between the lumen and a region surrounding the tubular member. Pressure sensing device may be configured to slide inside the intravascular device.

Furthermore, the pressure sensing device in method 300 may include a guide wire having a cable or other communication pathway to provide power and collect data from a component (e.g., a sensor). Likewise, the system in method 300 may include an interface device, a control console, and a display unit (e.g., interface device 230, control console 240, and display unit 250, cf. FIG. 5). Steps in method 300 may be partially performed by the control console using a processor circuit and a memory circuit included in the console (e.g., processor unit 242 and memory circuit 244, cf. FIG. 5).

In step 310 the intravascular device having openings extending along a distal portion is positioned inside a blood vessel. In step 320 a pressure sensing device is advanced through a lumen of the intravascular device to the distal portion of the intravascular device. In step 330, pressure measurements are obtained from the pressure sensing device while positioned within the distal portion of the intravascular device. In some embodiments, step 330 may include providing a voltage to a pressure sensing component of the pressure sensing device and/or providing an optical signal to an optical fiber in communication with the pressure sensing component. Accordingly, step 330 may be performed, at least partially, by the control console through the interface device.

A signal representative of the obtained pressure measurement is received from the pressure sensing device. For example, the signal may be received in the interface device. The signal from the pressure sensing device is processed. For example, in some embodiments an analogue signal may be converted to a digital signal in the interface device. A measurement is obtained or determined from the received and processed signal. These steps may be partially performed using the processor circuit and the memory circuit in the control console. In some embodiments, the processed signal from the pressure sensing device and a corresponding position of the pressure sensing device inside the blood vessel are stored in memory. For example, the processed signal and the position of the pressure sensing device may be stored in the memory circuit in the control console. In some embodiments, a representation of the pressure measurement is output to the display unit for display to a user.

The pressure sensing device can be displaced to a different position along the length of the intravascular device. This may include sliding the pressure sensing device in a distal or proximal direction relative to the distal tip of the intravascular device. Further, the displacement of the pressure sensing device can be tracked. For example, in some embodiments marks in the proximal end of the pressure sensing device and/or a linear encoder may indicate/track the displacement amount. In some instances, the intravascular deice includes spaced radiopaque markers along a distal portion that allows the tracking of the position of a radiopaque tip and/or markers of the pressure sensing device relative to the radiopaque markers of the catheter. In this manner, the data obtained by the pressure sensing device can be co-registered to the location of the pressure sensing device at the time the data was obtained. In some instances, the pressure measurements are obtained, continuously or periodically, as the pressure sensing device is moved along the length of the intravascular device.

Embodiments of the invention described above are exemplary only. One skilled in the art may recognize various alternative embodiments from those specifically disclosed. Those alternative embodiments are also intended to be within the scope of this disclosure. As such, the invention is limited only by the following claims.

What is claimed is:

1. An intravascular system, comprising:
    an intravascular device that includes:
        a tubular member having:
            a proximal portion and a distal portion configured to be positioned within a blood vessel of a patient;
            a lumen extending from the proximal portion to the distal portion along a longitudinal axis of the tubular member; and
            openings spaced along the distal portion of the tubular member, the openings sized and shaped to provide fluidic communication between the lumen and a region surrounding the tubular member; and
    a pressure sensor disposed at the distal portion of the tubular member such that the pressure sensor is configured to be positioned within the blood vessel, the pressure sensor sized and shaped to translate relative to the openings and within the lumen of the tubular member.

2. The system of claim 1, further comprising:
    an interface device configured to interface with a proximal portion of the pressure sensing device;
    a control console including a processor circuit and a memory circuit in communication with the interface device; and
        a display unit in communication with the control console.

3. The system of claim 1, wherein the pressure sensing device is a guide wire having an outer diameter of approximately 0.014 inches, 0.018 inches, or 0.035 inches.

4. The system of claim 1, wherein the openings include:
    a first pattern of openings; and
    a second pattern of openings, the second pattern circumferentially offset from the first pattern.

5. The system of claim 4, wherein the openings include a third pattern of openings, the third pattern circumferentially offset from the first pattern and the second pattern.

6. The system of claim 5, wherein the openings include a fourth pattern of openings, the fourth pattern circumferentially offset from the first pattern, the second pattern, and the third pattern.

7. The system of claim 6, wherein the first pattern, the second pattern, the third pattern, and the fourth pattern are equally spaced about the circumference of the tubular member.

8. The system of claim 4, wherein the first pattern of openings extends linearly along the longitudinal axis.

9. The system of claim 4, wherein the openings of the first pattern are spaced at regular intervals.

10. The system of claim 4, wherein the openings of the first pattern are spaced at irregular intervals.

11. The system of claim 1, wherein the openings are defined by elongated straight sides extending along the longitudinal axis and rounded ends.

12. The system of claim 1, wherein the tubular member includes a polymer tube.

13. The system of claim 12, wherein the tubular member further includes a reinforcement element.

14. The system of claim 13, wherein the reinforcement element is spiral ribbon coil embedded in the polymer tube.

15. The system of claim 13, wherein the reinforcement element is thin ribbon braid embedded in the polymer tube.

16. The system of claim 1, wherein the lumen has a diameter of approximately 0.016 inches.

17. The system of claim 1, wherein the distal portion of the tubular member includes a plurality of radiopaque markers spaced along a length of the tubular member.

18. A method for obtaining pressure measurements from an intravascular environment, the method comprising:
    disposing an intravascular device inside a blood vessel, the intravascular device including:
        a tubular member having:
            a proximal portion and a distal portion, wherein the distal portion is positioned within the blood vessel;
            a lumen extending from the proximal portion to the distal portion along a longitudinal axis of the tubular member; and
            openings spaced along the distal portion of the tubular member, the openings sized and shaped to provide fluidic communication between the lumen and a region surrounding the tubular member;
    advancing a pressure sensor relative to the openings and through the lumen of the tubular member to a position within the distal portion of the tubular member such that the pressure sensor is positioned within the blood vessel; and
    obtaining pressure measurements with the pressure sensor positioned within the distal portion of the tubular member.

19. The method of claim 18, further comprising displacing the pressure sensing device to a different position within the distal portion of the intravascular device while maintaining the position of the intravascular device relative to the blood vessel.

* * * * *